US00PP35518P2

(12) United States Plant Patent
McNamara et al.

(10) Patent No.: US PP35,518 P2
(45) Date of Patent: Dec. 5, 2023

(54) ***FORSYTHIA* PLANT NAMED 'UMNFOR01'**

(50) Latin Name: ***Forsythia* hybrid**
Varietal Denomination: UMNFOR01

(71) Applicant: Regents of the University of Minnesota, Minneapolis, MN (US)

(72) Inventors: Steven Thomas McNamara, Victoria, MN (US); Peter Christian Moe, Excelsior, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 18/116,099

(22) Filed: Mar. 1, 2023

Related U.S. Application Data

(63) Continuation of application No. 63/326,947, filed on Apr. 4, 2022.

(51) Int. Cl.
*A01H 5/02* (2018.01)
*A01H 6/00* (2018.01)

(52) U.S. Cl.
USPC ..... Plt./230
CPC ..... *A01H 6/00* (2018.05)

(58) Field of Classification Search
USPC ..... Plt./230
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Forsythia* plant named 'UMNFOR01' that is characterized by its heavy flower production in spring, its moderate growth rate and short internodes resulting in a dense, compact, and rounded plant shape, its small stature; reaching a mature height of about 1.52 m and a mature spread of about 1.82 m, and its flower buds that are hardy to U.S.D.A. Zone 5a and plant hardiness to U.S.D.A. Zone 4a.

2 Drawing Sheets

Genus/species: *Forsythia* hybrid.
Varietal denomination: 'UMNFOR01'.

BACKGROUND OF THE INVENTION

The present invention relates to a new and distinct *Forsythia* plant of hybrid origin and will be referred to hereafter by its cultivar name, 'UMNFOR01'. 'UMNFOR01' represents a new cultivar of *Forsythia*, a deciduous shrub grown for landscape use.

The new cultivar is the result of a controlled breeding program conducted by the Inventors at a research station in Donald, Oreg. The intent of the program was to develop new *Forsythia* cultivars that combine superior cold tolerance and excellent floral and foliar characteristics on compact, small-statured plants.

The new cultivar arose from open-pollinated plants of *Forsythia* 'Northern Sun' (not patented) that was growing amongst other *Forsythia* cultivars at a research station in Donald, Oreg. in 1998. The male parent is therefore unknown. 'UMNFOR01' was selected as a single unique plant from the resulting seedlings in spring of 2004.

Asexual propagation of the new cultivar was first accomplished by softwood cuttings in Donald, Oreg. in summer of 2004 by one of the Inventors. Asexual propagation by softwood stem cuttings has determined the new cultivar is stable and reproduced true to type in successive generations.

SUMMARY OF THE INVENTION

The following traits have been repeatedly observed and represent the characteristics of the new cultivar and distinguish 'UMNFOR01' as a unique cultivar of *Forsythia*.

1. 'UMNFOR01' exhibits heavy flower production in spring.
2. 'UMNFOR01' exhibits a moderate growth rate and short internodes resulting in a dense, compact, and rounded plant shape.
3. 'UMNFOR01' exhibits small stature; reaching a mature height of about 1.52 m (5 ft) and a spread of about 1.82 m (6 ft).
4. 'UMNFOR01' exhibits flower buds that are hardy to U.S.D.A. Zone 5a and plant hardiness to U.S.D.A. Zone 4a.

The female parent of 'UMNFOR01' is similar to 'UMNFOR01' in having an abundance of 4-lobed bright yellow color flowers in early spring and medium to dark green color foliage. The female parent of 'UMNFOR01' differs from 'UMNFOR01' in having a larger plant size, longer internodes, a more open and less compact plant habit, flower buds that are more cold hardy, and in requiring more pruning to maintain an attractive plant form in the landscape. 'UMNFOR01' can also be compared to the *Forsythia* cultivar 'Nimbus' (U.S. Plant Pat. No. 23,838). 'Nimbus' differs from 'UMNFOR01' in having a much more dwarf plant habit and in blooming only in mild winters in Minnesota.

BRIEF DESCRIPTION OF THE DRAWINGS

The accompanying color photographs illustrate the overall appearance and distinct characteristics of the new *Forsythia*. The photographs were taken of a 5-year-old plant of 'UMNFOR01' as grown outdoors in a trial field in Newport, Minn.

The photograph in FIG. 1 provides a side view of a plant of 'UMNFOR01' in bloom.

Figure 1:
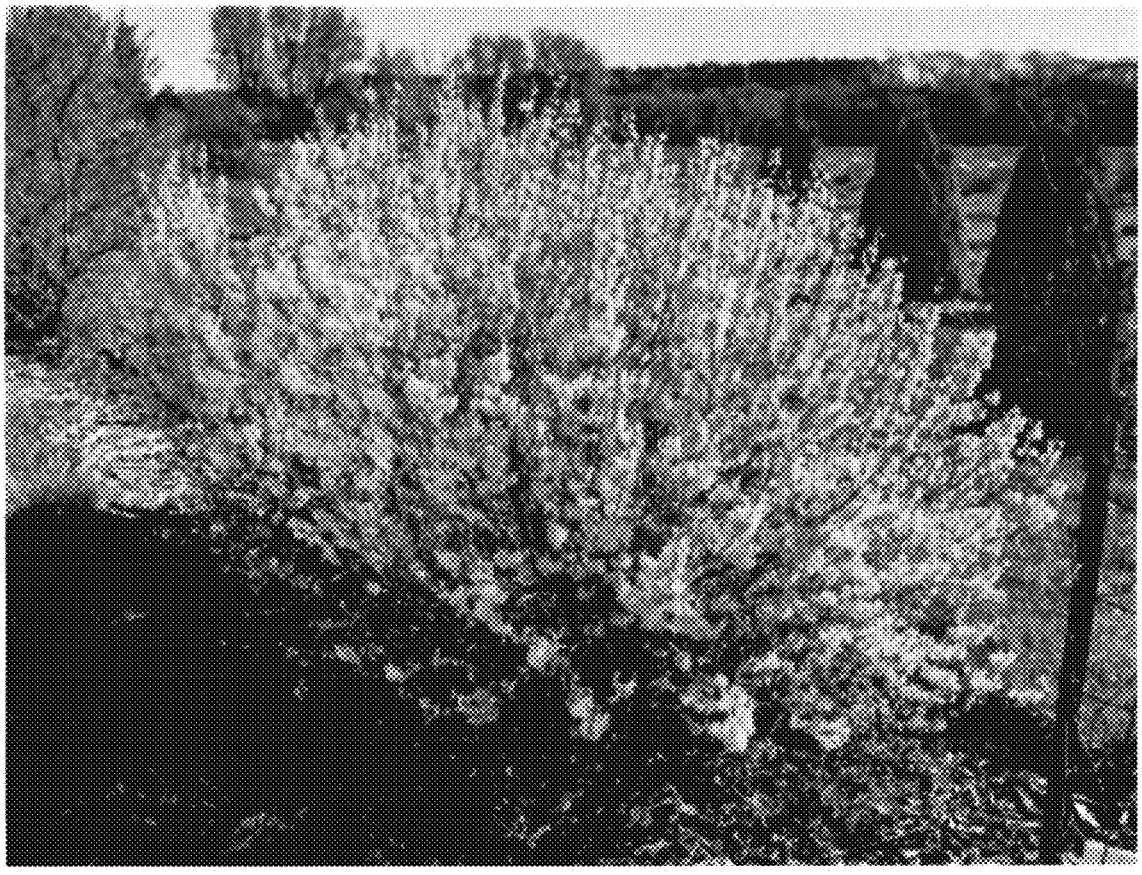
Figure 2:
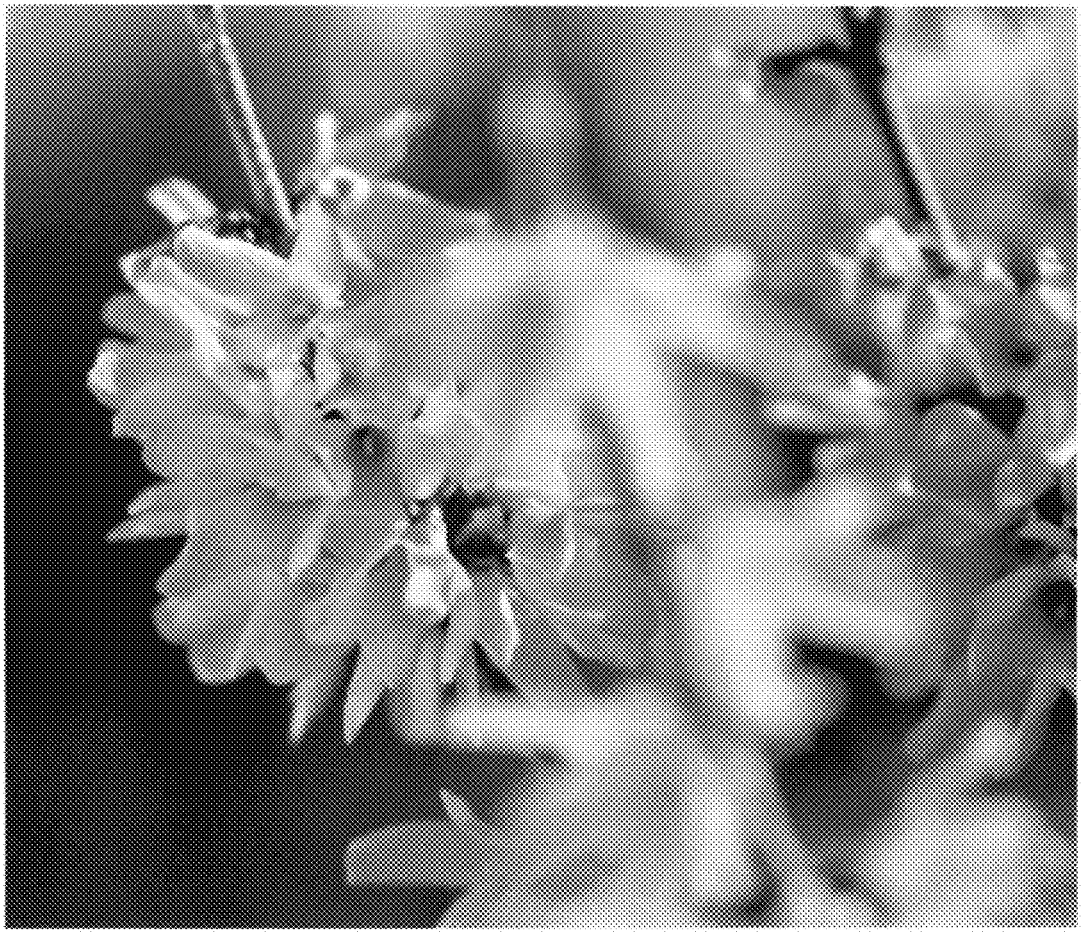

The photograph in FIG. 2 provides a close-up view of the flowers of 'UMNFOR01'.

The colors in the photographs are as close as possible with the photographic and printing technology utilized and the color values cited in the detailed botanical description accurately describe the colors of the new *Forsythia*.

DETAILED BOTANICAL DESCRIPTION

The following is a detailed description of 3-year-old plants of 'UMNFOR01' as grown outdoors in one-gallon containers in Excelsior, Minn. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms heavily for 2 weeks in early spring in Minnesota following moderate (U.S.D.A. Zone 5a) winter temperature conditions.

*Plant type*.—Deciduous shrub.

*Plant habit*.—Compact, dense, rounded, small stature.

*Height and spread*.—50 cm in height and 78 cm in spread as grown in a 1-gallon container, reaching a mature height of about 1.52 m and a spread of about 1.82 m in the landscape.

*Cold hardiness*.—Flower buds that are hardy to at least U.S.D.A. Zone 5a and plant hardiness to at least U.S.D.A. Zone 4a.

*Diseases and pests*.—No susceptibility or resistance to diseases or pests has been observed.

*Root description*.—Fibrous and fine, 162D in color.

*Propagation*.—Softwood stem cuttings.

*Time required for root initiation*.—Root initiation occurs in 4 weeks, a young marketable plant is produced in about 2 years.

*Growth rate*.—Moderate.

Stem description:

*Stem shape*.—Round, solid.

*Stem color*.—Young stems; 144B and 151B, mature stems; 161A, older wood and bark; 198B.

*Stem size*.—Trunk; average of 1.2 cm in diameter, 2 cm in length, main branches grow from base; average of 4 mm in diameter, 48 cm in length, lateral branches; average of 3 mm in diameter and 10 cm in length.

*Stem surface*.—Young stems; smooth, glabrous, slightly glossy, mature stems; matte and densely covered with lenticels an average of 20 per cubic cm, 1.5 mm in width, 0.5 mm in height, 165A in color, older wood and bark; matte and densely covered with lenticels; an average of 20 per cubic cm, an average of 1.5 mm in width and 0.5 mm in height, 200A in color.

*Internode length*.—Average of 5.5 cm.

*Branch quantity*.—Average of 14 main branches growing off trunk, typically 6 secondary branches on a main branch (often in opposite pairs).

Foliage description:

*Leaf shape*.—Ovate.

*Leaf division*.—Simple.

*Leaf base*.—Ovate.

*Leaf apex*.—Cuneate.

*Leaf venation*.—Pinnate, upper surface; mostly non-conspicuous except center main vein 144A, lower surface; not conspicuous.

*Leaf margins*.—Serrated.

*Leaf attachment*.—Petiolate.

*Dormant vegetative buds*.—Conical, obovate with pointed apex, average of 5 mm in length, 1.5 mm in width at the widest point.

*Leaf arrangement*.—Opposite.

*Leaf surface*.—Glabrous and matte on both surfaces.

*Leaf size*.—6.5 cm in length, 3 cm in width.

*Leaf color*.—Young and mature leaves; upper surface NN137B, margins 145B, lower surface 148B.

*Petiole*.—An average of 1.2 cm in length and 1.1 mm in width.

*Stipules*.—Very small in size average of 1.2 mm in length and diameter, at base of petioles, remains as buds (not leafy), N167A and 200A.

Flower description:

*Inflorescence type*.—Flowers are solitary in groups of 1 to 7.

*Natural flowering season*.—Early spring in Newport, Minn.

*Flowering habit*.—Not repeating; very floriferous.

*Pedicel*.—Average of 7 mm in length, 1 mm in width, 144A in color.

*Flower buds*.—Narrow oblong in shape, acute apex, 8 mm in length and 3 mm in diameter, 144C in color.

*Flower type*.—Single, ranging from nearly salverform to somewhat bell shaped.

*Flower lastingness*.—Approximately 2 weeks, not persistent.

*Flower aspect*.—Vertical to stem and very slightly drooping.

*Fragrance*.—Very slightly fragrant, pleasant.

*Calyx*.—4-lobed, somewhat conical, fused at base, 4 mm in diameter at the top, tapering down to 1 mm in diameter, 144B in color, 187B at apex, fringed with short white hairs.

*Sepals*.—Rotate in arrangement, fused at the base, 3 mm in length, 2 mm in width, ovate in shape, entire margins, not undulate, acute apex, surfaces smooth, glabrous, slightly glossy, color; both surfaces 144C, apex 183A.

*Petals*.—4 petals, evenly spaced around the perimeter of corolla, bluntly acute to rounded apex, 30% of base fused, 1.7 cm in length, 5 mm in width, entire and somewhat undulate margins, reflexed from the central axis of the petal, color: when opening and fully open upper (inner) surface; 6A, base with striped parallel venation N25B, when opening and fully open lower (outer) surface; 6A.

Reproductive organs:

*Androecium*.—Stamens; 2, anther; fused together, oblong in shape, an average of 2 mm in length, 1.2 mm in width, 14A in color, filaments; average of 5 mm in length, 0.4 mm in width, pollen; abundant, 14A in color.

*Gynoecium*.—Pistil; 1, minute, stigma; minute, round in shape, 0.3 mm in diameter, 144C in color, style; average of 1.5 mm in length, 0.5 mm in width, ovary; inferior, round in shape, 1.5 mm in diameter, 144A in color.

Fruit and seed: Fruit and seeds have not been observed to date.

It is claimed:

1. A new and distinct cultivar of *Forsythia* plant named 'UMNFOR01' as herein illustrated and described.

* * * * *